US012727754B2

(12) United States Patent
Yazdi et al.

(10) Patent No.: US 12,727,754 B2
(45) Date of Patent: Sep. 8, 2026

(54) METHODS AND SYSTEMS FOR UPGRADABLE VIDEO MEDICAL DEVICE SYSTEM

(71) Applicant: Verathon Inc., Bothell, WA (US)

(72) Inventors: Reza Ahmadian Yazdi, Coquitlam (CA); Daniel Roodnick, Delta (CA); Willie Mah, North Vancouver (CA); Xiaoping Liu, Coquitlam (CA); Rohan Sidhu, Abbotsford (CA)

(73) Assignee: Verathon Inc., Bothell, WA (US)

( * ) Notice: Subject to any disclaimer, the term of this patent is extended or adjusted under 35 U.S.C. 154(b) by 346 days.

(21) Appl. No.: 18/541,775

(22) Filed: Dec. 15, 2023

(65) Prior Publication Data

US 2024/0108207 A1 Apr. 4, 2024

Related U.S. Application Data

(62) Division of application No. 17/036,944, filed on Sep. 29, 2020, which is a division of application No.
(Continued)

(51) Int. Cl.
*A61B 1/267* (2006.01)
*A61B 1/00* (2006.01)
(Continued)

(52) U.S. Cl.
CPC .......... *A61B 1/267* (2013.01); *A61B 1/00006* (2013.01); *A61B 1/0002* (2013.01); *A61B 1/00045* (2013.01); *A61B 1/00059* (2013.01); *A61B 1/00114* (2013.01); *A61B 1/045* (2013.01); *H04N 23/56* (2023.01); *H04N 23/76* (2023.01); *A61B 1/00009* (2013.01); *A61B 1/00103* (2013.01); *A61B 1/05* (2013.01);
(Continued)

(58) Field of Classification Search
CPC .............................. A61B 1/267; A61B 1/2673
See application file for complete search history.

(56) References Cited

U.S. PATENT DOCUMENTS

| | | | |
|---|---|---|---|
| 4,967,269 | A | 10/1990 | Sasagawa et al. |
| 5,091,779 | A | 2/1992 | Ams et al. |

(Continued)

FOREIGN PATENT DOCUMENTS

| | | | |
|---|---|---|---|
| CA | 2689676 | C | 8/2013 |
| JP | 2011176671 | A | 9/2011 |
| WO | 2014190879 | A1 | 12/2014 |

*Primary Examiner* — Olivia C Chang
(74) *Attorney, Agent, or Firm* — Duane Morris LLP

(57) ABSTRACT

A method for updating image capture settings of a video medical device, comprises connecting the video medical device to a video monitor via a data cable, wherein two or more of the video medical device, the video monitor, and the data cable each include storage for storing image capture settings. It is determined which of the video medical device, the video monitor, or the data cable have a most up-to-date set of image capture settings for an identified video medical device. The most up-to-date set of image capture settings is forwarded to the video medical device when it is determined that one of the video monitor or the data cable include the most up-to-date set of image capture settings. The stored image capture settings on the video medical device are updated based on the received most up-to-date set of image capture settings.

11 Claims, 9 Drawing Sheets

Related U.S. Application Data

15/864,416, filed on Jan. 8, 2018, now Pat. No. 10,820,792.

(60) Provisional application No. 62/444,181, filed on Jan. 9, 2017.

(51) Int. Cl.

| | |
|---|---|
| ***A61B 1/045*** | (2006.01) |
| ***H04N 23/56*** | (2023.01) |
| ***H04N 23/76*** | (2023.01) |
| *A61B 1/05* | (2006.01) |
| *A61B 1/06* | (2006.01) |
| *A61B 90/00* | (2016.01) |
| *H04N 23/50* | (2023.01) |

(52) U.S. Cl.

CPC ........... *A61B 1/0676* (2013.01); *A61B 1/0684* (2013.01); *A61B 2090/0803* (2016.02); *H04N 23/555* (2023.01)

(56) References Cited

U.S. PATENT DOCUMENTS

| | | | |
|---|---|---|---|
| 6,147,705 | A | 11/2000 | Krauter et al. |
| 6,414,708 | B1 | 7/2002 | Carmeli et al. |
| 6,462,770 | B1 | 10/2002 | Cline et al. |
| 6,724,418 | B1 | 4/2004 | Takahashi |
| 6,747,808 | B2 | 6/2004 | Voss et al. |
| 6,767,321 | B2 | 7/2004 | Czarnek et al. |
| 6,809,499 | B2 | 10/2004 | Solingen |
| 6,943,822 | B2 | 9/2005 | Lida et al. |
| 7,136,098 | B1 | 11/2006 | Burnett et al. |
| 7,247,135 | B2 | 7/2007 | Iriyama |
| 7,289,140 | B2 | 10/2007 | Kobayashi |
| 7,319,478 | B2 | 1/2008 | Dolt et al. |
| 7,573,499 | B2 | 8/2009 | Doguchi et al. |
| 7,670,286 | B2 | 3/2010 | Imaizumi et al. |
| 8,027,533 | B2 | 9/2011 | Li et al. |
| 8,149,274 | B2 | 4/2012 | Yamazaki |
| 8,199,188 | B2 | 6/2012 | Amling et al. |
| 8,233,038 | B2 | 7/2012 | Iketani et al. |
| 8,427,534 | B2 | 4/2013 | Tashiro |
| 8,537,210 | B2 | 9/2013 | Omori et al. |
| 8,624,966 | B2 | 1/2014 | Ozawa et al. |
| 8,860,793 | B2 | 10/2014 | Lo et al. |
| 8,885,033 | B2 | 11/2014 | Masaki et al. |
| 8,944,596 | B2 | 2/2015 | Wood et al. |
| 8,947,514 | B2 | 2/2015 | Shibasaki |
| 8,972,714 | B2 | 3/2015 | Talbert et al. |
| 2007/0142707 | A1 | 6/2007 | Wiklof et al. |
| 2011/0130627 | A1 | 6/2011 | McGrail et al. |
| 2011/0193948 | A1 | 8/2011 | Amling et al. |
| 2013/0016200 | A1 | 1/2013 | Ovod |
| 2015/0116470 | A1 | 4/2015 | Ovod |
| 2016/0226272 | A1 | 8/2016 | McGrath et al. |
| 2016/0242637 | A1 | 8/2016 | Tydlaska et al. |

METHODS AND SYSTEMS FOR UPGRADABLE VIDEO MEDICAL DEVICE SYSTEM

CROSS-REFERENCE TO RELATED APPLICATION

This application is a divisional of U.S. patent application Ser. No. 17/036,944 filed Sep. 29, 2020, which is a divisional of U.S. patent application Ser. No. 15/864,416 filed Jan. 8, 2018, which claims priority under 35 U.S.C. § 119 based on U.S. Provisional Patent Application No. 62/444,181, filed Jan. 9, 2017, the disclosures of which are hereby incorporated by reference herein.

BACKGROUND

Endotracheal intubation provides the current preferred method for control of the airway for mechanical ventilation. The process involves passing an endotracheal tube (ETT) through the mouth, past the tongue, and to and through the vocal cords and larynx to seal the airway. This protects the openness of the airway and protects the airway from aspiration of gastric contents, foreign substances, or secretions.

Traditional laryngoscopes rely on opening the upper airway to provide a direct line of sight from the medical practitioner's eye to the larynx. Subsequent developments in laryngoscopes utilized fiberoptic bundles, sometimes coupled to video displays. More recently, laryngoscopes with video cameras have made it possible to display the image of the airway anatomy from a remote position, and in some instances allow the intubator to identify the relevant anatomical landmarks without repositioning the patient. This technology reduces the past problem of difficult intubation when the glottis entrance cannot be adequately seen and further reduces the likelihood of infection by medical personnel being unduly close to the nose and mouth of the patient can be avoided.

Unfortunately, image quality and consistency have reduced the utility of video laryngoscopes and have caused many practitioners to revert to traditional, direct view laryngoscopes.

DETAILED DESCRIPTION OF THE PREFERRED EMBODIMENTS

Figure 1:
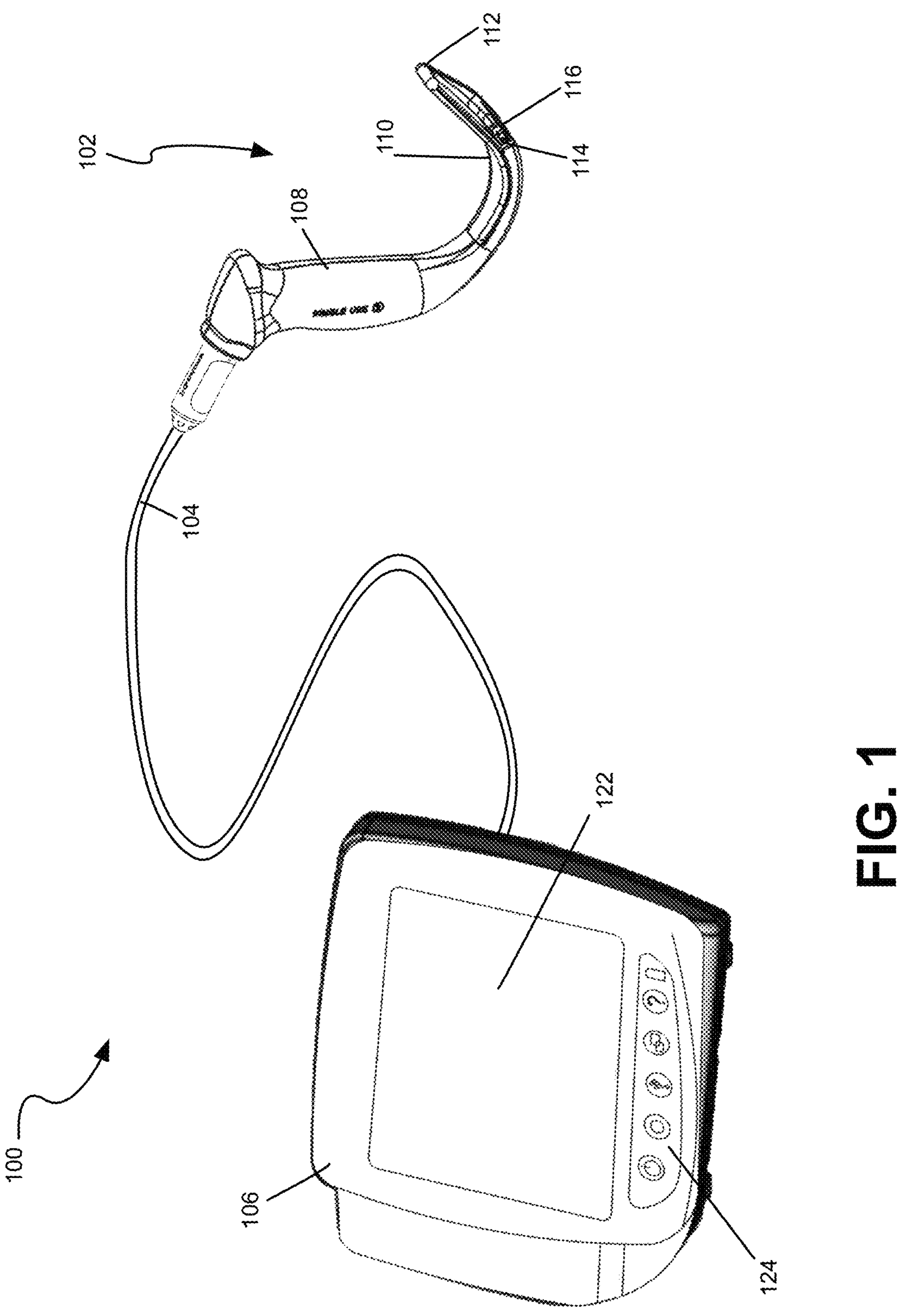
FIG. 1 is a diagram illustrating a laryngoscope system consistent with embodiments described herein.

The following detailed description refers to the accompanying drawings. The same reference numbers in different drawings may identify the same or similar elements. Also, the following detailed description does not limit the invention.

Several embodiments of a video-based intubation laryngoscope and system are described that allow for examination of the upper airway during intubation. The system employs video laryngoscope embodiments configured to view a patient's glottis, reposition the patient's epiglottis, view the glottic aperture and convey video images of the patient's upper airway anatomy including the glottis and/or glottic aperture and surrounding area to a video monitor viewable by the laryngoscope user.

Embodiments of the laryngoscope include both single-use (i.e., disposable) and reusable laryngoscope blades that include image capturing and lighting elements. The blade is used to reposition the epiglottis by engagement of the patient's vallecula, or alternatively, directly lifting the epiglottis to reveal the glottic aperture. During and after insertion of the blade, into the patient's upper airway, images obtained from the image capturing elements are conveyed to a video monitor viewable by the laryngoscope user via a data cable. Improved intubation speed and accuracy are accomplished by providing unobstructed, real time or "live" views that are immediately viewable on the video monitor.

Consistent with embodiments described herein, the laryngoscope blade, the data cable, and the video monitor may each include logic components configured to enable image data to be exchanged between the image capturing element and the video monitor in an efficient and optimized manner.

In exemplary embodiments, the laryngoscope blade may include logical components for authenticating the blade with other components in the system (e.g., the video monitor and/or data cable) and logging use of the laryngoscope blade (e.g., number of times used, dates/times, etc.), and for negotiating with other components in the laryngoscope system (e.g., the blade and the video monitor) to determine which component has the most up-to-date software, which may include optimized camera settings and other instructions relevant to the particular laryngoscope blade.

In one exemplary embodiment relating to disposable laryngoscope blades, one or more components of the image capturing element may be included within the data cable, thus rendering the remaining image capturing components in the laryngoscope blade less expensive, which is particularly advantageous for a single use device. In such an embodiment, the data cable may include one or more logical components configured to identify when a laryngoscope blade has been connected, which blade has been connected (e.g., type of blade, particular blade, etc.), and to negotiate with other components in the laryngoscope system (e.g., the blade and the video monitor) to determine which component has a most up-to-date software, which may include optimized camera settings and other instructions relevant to the identified laryngoscope blade.

In other embodiments, such as reusable laryngoscope blades, the logical components of the data cable may be integrated within the laryngoscope blade and negotiation may take place between the laryngoscope blade and the video monitor.

As briefly described above, exemplary embodiments of the laryngoscope system facilitate the exchange of optimized camera settings between system components. As described in detail below, such optimized camera settings may be specific to each type of laryngoscope blade and may enable the video camera elements within the laryngoscope blade to capture images having a reduced amount of far field dimming in the event that a portion of the patient's anatomy partially obscures the camera view. This allows practitioners to ascertain the relevant anatomy, even where such anatomy is the far field of the image.

Figure 2A:
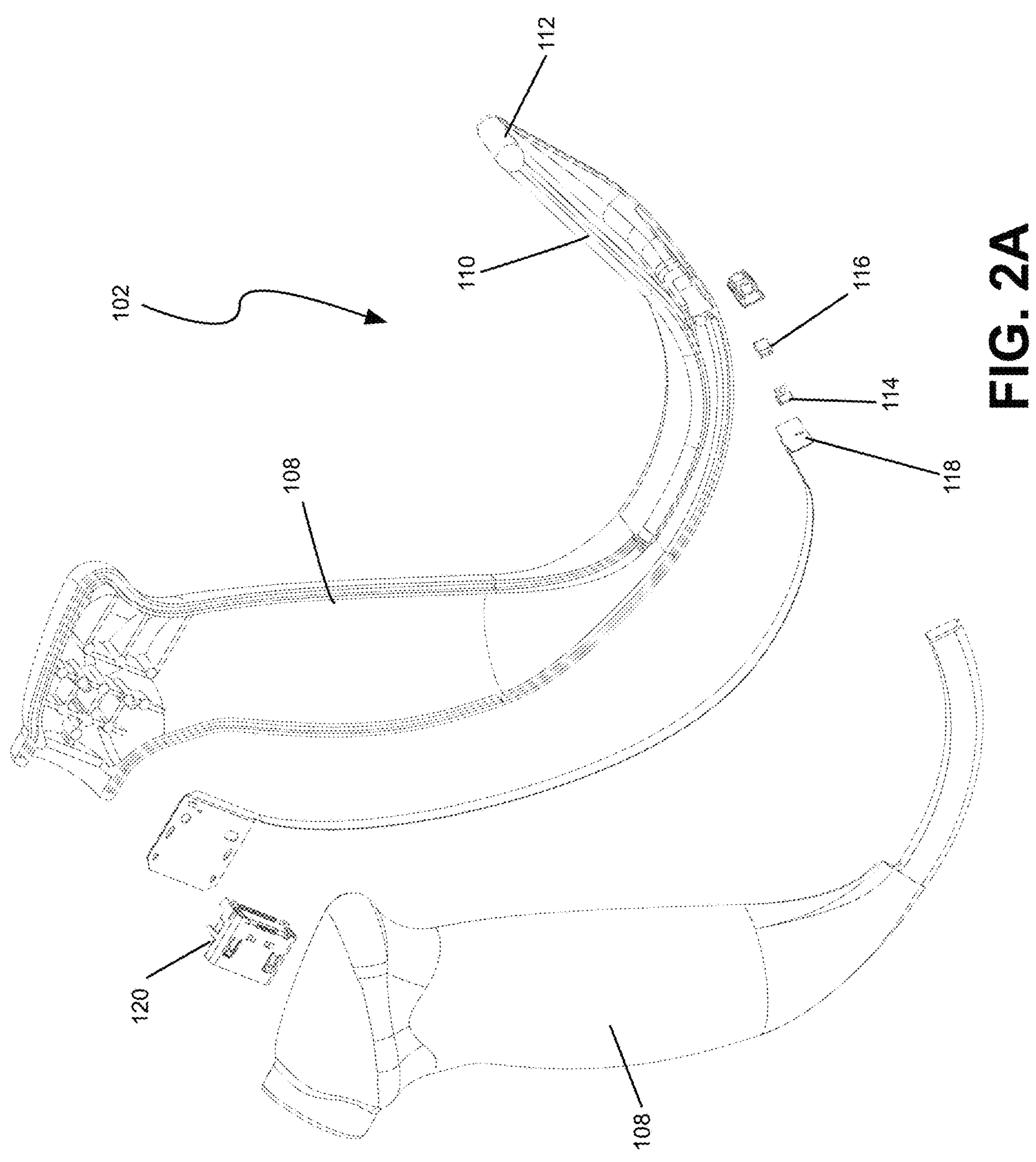
FIG. 2A is an exploded front isometric view of the laryngoscope blade of FIG. 1.
Figure 2C:
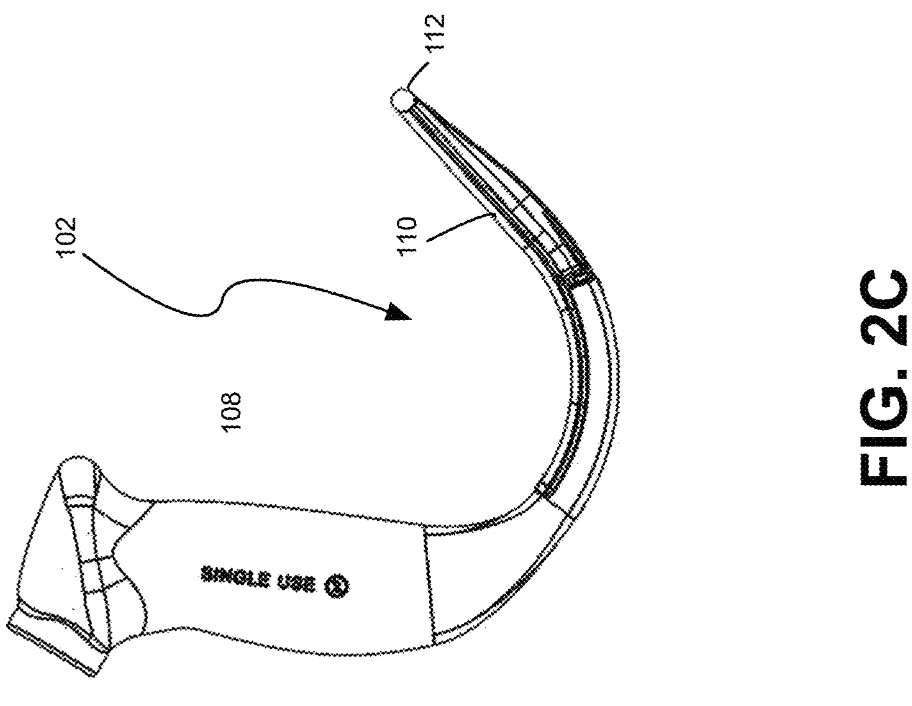
FIG. 2C is a side plan view of the laryngoscope blade of FIG. 2A.
Figure 2B:
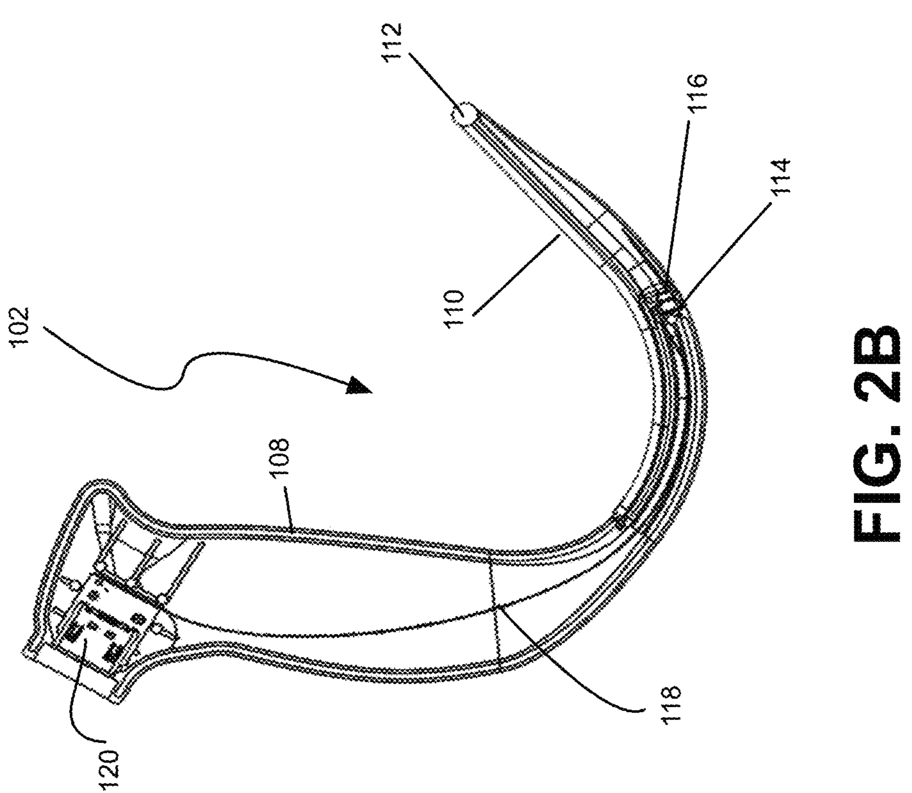
FIG. 2B is a side cross-sectional view of the laryngoscope blade of FIG. 2A.

FIG. 1 illustrates a video laryngoscope system 100 consistent with implementations described herein. As shown, video laryngoscope system 100 comprises a laryngoscope blade 102, a data cable 104, and a video monitor 106. FIG. 2A is an exploded front perspective view of a single-use laryngoscope blade 102 configured in accordance with embodiments described herein. FIGS. 2B-2E are an assembled front perspective view, side view, front view, and rear view of blade 102, respectively.

Figure 2E:
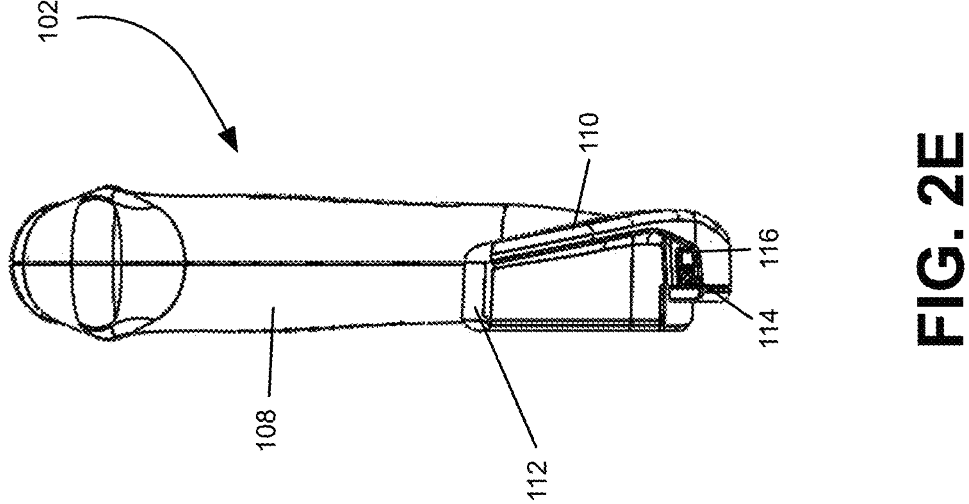
FIG. 2E is a rear plan view of the laryngoscope blade of FIG. 2A.
Figure 2D:
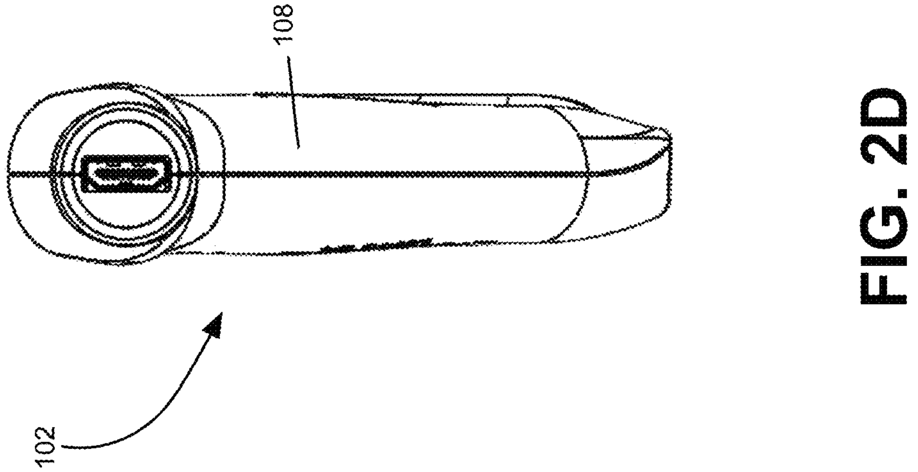
FIG. 2D is a front plan view of the laryngoscope blade of FIG. 2A.

As shown in FIGS. 1-2E, laryngoscope blade 102 includes a handle portion 108, a blade portion 110, a distal tip 112, a camera module 114, a light source module 116, a flexible printed circuit board (PCB) 118, and a cable interface 120.

During use, distal tip 112 is used for lifting the epiglottis or for engaging the vallecula of a patient to lift the epiglottis to reveal the glottic aperture. Camera module 114 and light source module 116 are positioned on a posterior side of the blade portion 110 and are directed towards the distal tip 112 so as to capture and transmit images of the distal tip 112 and corresponding patient anatomy to video monitor 106 via data cable 104.

Camera module 114 may include charge-coupled device (CCD) or Complementary Metal Oxide Silicon (CMOS) configurations that may be placed at a point of angulation of blade portion 110 near its midpoint to provide for advantageous positioning of camera module 114 at some distance from the glottic opening to allow a degree of perspective and wide angle viewing. Light source module 116 may include a light emitting diode (LED) lighting array.

As shown in FIG. 2A, flexible PCB 118 may be configured to couple cable interface 120 to camera module 114 and light source module 116 and may further include or more processors or memory devices, as described below. In other embodiments, PCB 118 may include two or more distinct PCBs joined by wires or other elements.

As described briefly above, in some embodiments data cable 104 may include one or more components of the image capturing element, such as a serializer component. In such an embodiment, the data cable 104 may further include one or more logical components configured to identify when a laryngoscope blade has been connected, which blade has been connected, and to negotiate with video monitor 106 to determine which of the data cable 104 and the video monitor 106 have the most up-to-date camera settings for use during image capture. In such a single-use blade embodiment, the combination of the data cable 104 and the laryngoscope blade 106 may together perform functions corresponding to reusable laryngoscope.

Video monitor 106 may provide power to and initiate image capture from laryngoscope blade 102 via data cable 104. For example, as shown in FIG. 1, video monitor 106 may include a display 122, and a control pad 124. Practitioners (e.g., medical personnel) may interface with video monitor 106 during use to initiate image capture, freeze a particular frame, or adjust certain limited settings. Although not shown in the Figures, video monitor 106 may also include a data cable interface for receiving an end of data cable 104, a battery or other power source, and a remote monitor interface for enabling the view of display 122 to be transmitted to one or more other display monitors.

Figure 3:
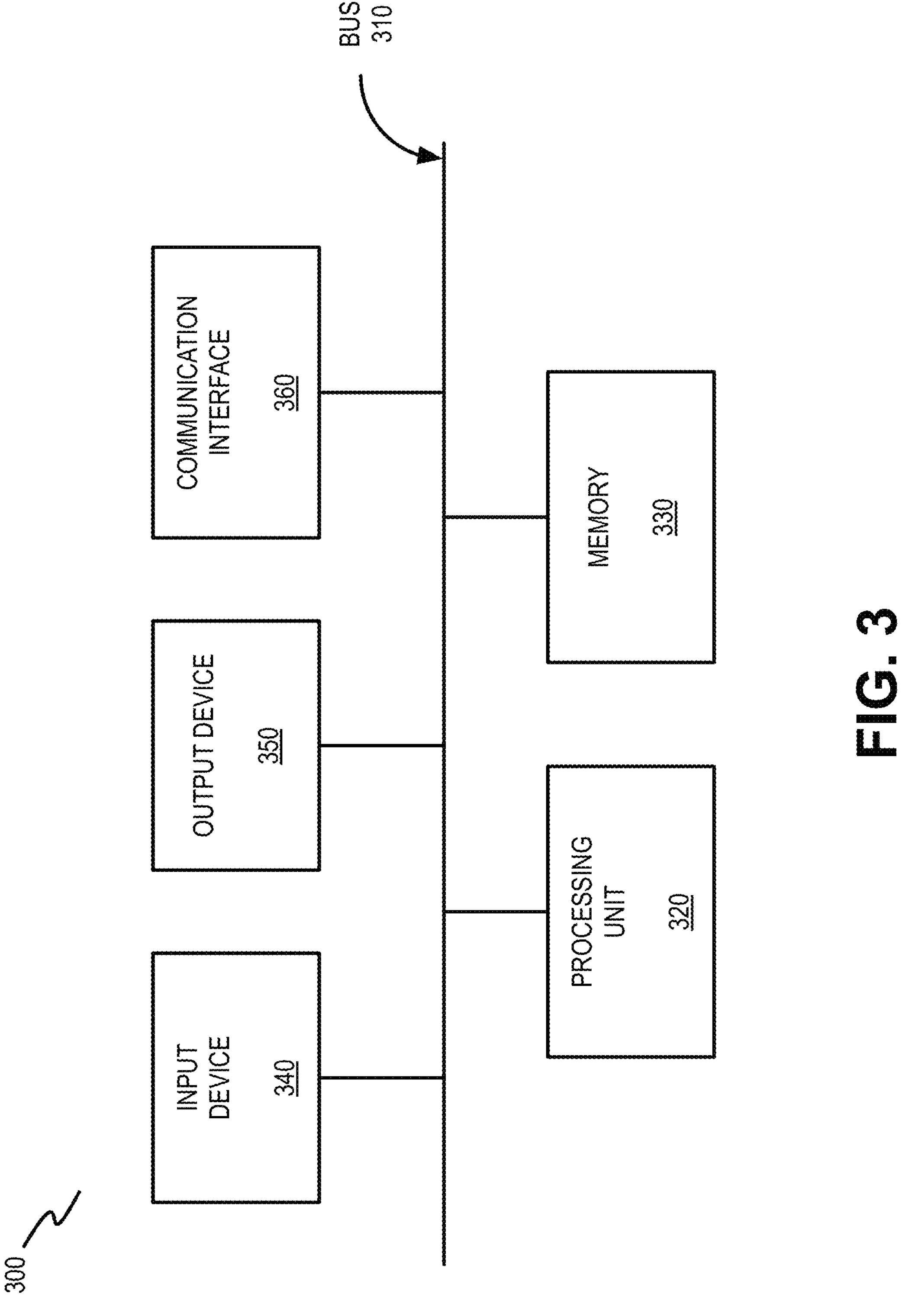
FIG. 3 illustrates a simplified exemplary configuration of one or more components of the laryngoscope system of FIG. 1.

FIG. 3 illustrates a simplified exemplary configuration of one or more components 300 of laryngoscope system 100, such as laryngoscope 102, data cable 104, and video monitor 106. Referring to FIG. 3, component 300 may include bus 310, a processing unit 320, a memory 330, an input device 340, an output device 350, and a communication interface 360. Bus 310 may include a path that permits communication among the components 300 of laryngoscope system 100. In one exemplary implementation, bus 310 may include an $I^2C$ bus which supports a master/slave relationship between components 300. As described below, in exemplary implementations, the master and slave roles may be negotiated between the components.

Processing unit 320 may include one or more processors, microprocessors, or processing logic that may interpret and execute instructions. Memory 330 may include a random access memory (RAM) or another type of dynamic storage device that may store information and instructions for execution by processing unit 320. Memory 330 may also include a read only memory (ROM) device (e.g., an electrically erasable and programmable ROM (EEPROM)) or another type of static storage device that may store static information and instructions for use by processing unit 320. In other embodiments, memory 330 may further include a solid state drive (SDD).

Input device 340 may include a mechanism that permits a user to input information to laryngoscope system 100, such as a keyboard, a keypad, a mouse, a pen, a microphone, a touch screen, voice recognition and/or biometric mechanisms, etc. Output device 350 may include a mechanism that outputs information to the user, including a display (e.g., a liquid crystal display (LCD)), a printer, a speaker, etc. In some implementations, a touch screen display may act as both an input device and an output device. In the laryngoscope system 100 depicted in FIG. 1, only video monitor 106 may be provided with input device 340 and output device 350, however in other implementations, one or more other components of laryngoscope system 100 may include such devices. As depicted in FIG. 1, laryngoscope blade 102 and data cable 104 may be implemented as headless devices that are not directly provided with input device 340 or output device 350 and may receive commands from, for example, video monitor 106.

Communication interface 360 may include one or more transceivers that laryngoscope system 100 (e.g., video monitor 106) uses to communicate with other devices via wired, wireless or optical mechanisms. For example, communication interface 360 may include a modem or an Ethernet interface to a local area network (LAN) or other mechanisms for communicating with elements in a communication network (not shown in FIG. 1). In other embodiments, communication interface 360 may include one or more radio frequency (RF) transmitters, receivers and/or transceivers and one or more antennas for transmitting and receiving RF data via a communication network, such as a wireless LAN or Wi-Fi network.

The exemplary configuration illustrated in FIG. 3 is provided for simplicity. It should be understood that laryngoscope system 100 may include more or fewer components than illustrated in FIG. 3. In an exemplary implementation, laryngoscope system 100 performs operations in response to one or more processing units 320 executing sequences of instructions contained in a computer-readable medium, such as memory 330. A computer-readable medium may be defined as a physical or logical memory device. The software instructions may be read into memory 330 from another computer-readable medium (e.g., a hard disk drive (HDD), SSD, etc.), or from another device via communication interface 360. Alternatively, hard-wired circuitry may be used in place of or in combination with software instructions to implement processes consistent with the implementations described herein. Thus, implementations described herein are not limited to any specific combination of hardware circuitry and software.

Figure 4:
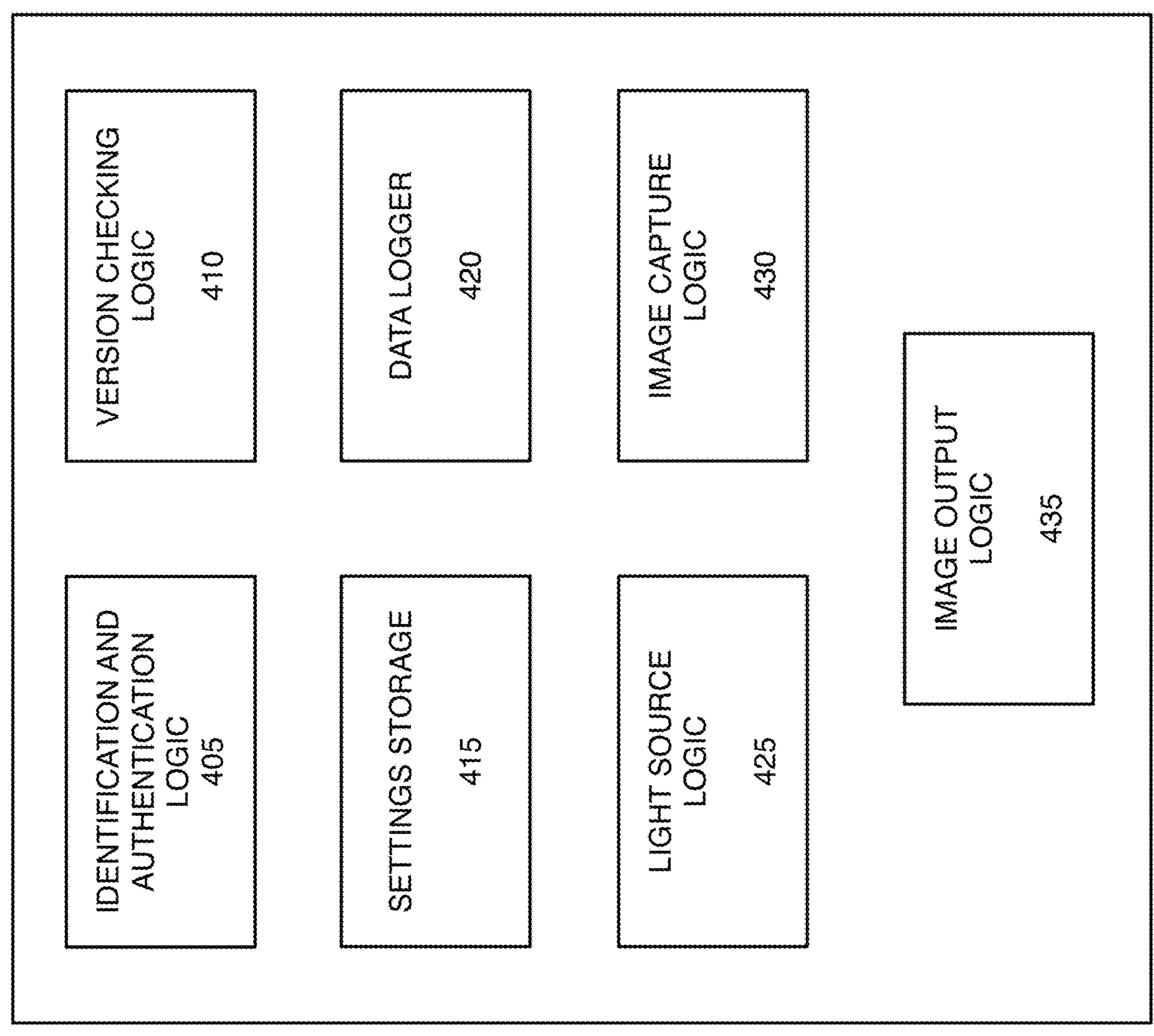
FIG. 4 is an exemplary functional block diagram of components implemented in a single-use laryngoscope blade consistent with embodiments described herein.

FIG. 4 is an exemplary functional block diagram of components implemented in a single-use laryngoscope blade 102 in accordance with an embodiment described herein. In the embodiment of FIG. 4, all or some of the components may be implemented by processing unit 320 executing software instructions stored in memory 330.

As shown, laryngoscope blade 102 may include identification and authentication logic 405, version checking logic 410, settings storage 415, data logger 420, light source logic 425, image capture logic 430, and image output logic 435.

Identification and authentication logic 405 is configured to, upon power up of laryngoscope blade 102, exchange identification and authentication information with data cable 104 and/or video monitor 106. For example, laryngoscope blade 102 may communicate identification information to data cable 104 via bus 310 (e.g., the $I^2C$ bus). In one embodiment, the identification information may comprise information relating to the type of laryngoscope blade 102, such as the size, application, model, etc. In other implementations, the identification information may include information specific to the particular laryngoscope blade 102, such as serial number or other uniquely identifying information.

Consistent with embodiments described herein, identification and authentication logic 405 may provide the identifying information to data cable 104 and video monitor 106 for use in determining whether laryngoscope blade 102 is authorized for use with the data cable 104 and video monitor 106. For example, as described below, upon receipt of the identification information from laryngoscope blade 102, the data cable 104 and/or video monitor 106 may determine whether the laryngoscope blade 102 is authorized for use. In this manner, unauthorized, third party laryngoscope blades may not be improperly used with the laryngoscope system described herein.

Furthermore, in other embodiments, identification and authentication logic 405 may be configured to exchange usage information stored in data logger 420 with video monitor 106 via data cable 104. For example, data logger 420 may be configured to record details regarding usage (e.g., power up) of the laryngoscope blade 102, such as date, time, and duration of laryngoscope blade 102. Identification and authentication logic 405 may, during subsequent power ups, transmit this information to video monitor 106 to for use in determining whether the laryngoscope blade 102 may be properly used. For example, single-use blades may only be authorized for power-up a predetermined (e.g., <5) number of times, to ensure that the blades are not used outside of their intended purpose. For reusable blades, the usage information stored in data logger 420 may be used to provide historical information, reconditioning recommendations, etc. In other embodiments, the information may be used to monitor a time between uses, to determine whether appropriate sterilization procedures have been followed.

Version checking logic 410 is configured to, in coordination with similar logic in data cable 104 and video monitor 106, determine which component has a most recently updated set of camera settings. For example, because components of medical devices may not be upgradable in the field, providing an integrated upgrade path within the separate components provides an efficient manner for rolling out updated camera settings using only a single factory-updated component, without requiring a dedicated field update process.

Consistent with embodiments described herein, upon power up of system 100, version checking logic 410 determines which of laryngoscope blade 102, data cable, 104, or video monitor 106 maintains the most recently updated set of camera settings in settings storage 415. If laryngoscope blade 102 is not the device with the most recently updated set of camera settings, the device having such settings may transmit the camera settings to laryngoscope blade 102 or otherwise make the settings available to image capture logic 430.

As described briefly above, in one embodiment, laryngoscope blade 102, data cable, 104, and video monitor 106 may be coupled via an $I^2C$ bus, which requires that only one device be in the "master" role at any one time. Generally, since the main control of system 100 is initiated by video monitor 106, video monitor 106 is typically in the "master" role. However, consistent with embodiments described herein, upon system power up, each of video monitor 106, data cable 104, and/or laryngoscope blade 102 may alternatively assume the "master" role for the purposes of sharing information regarding its set of camera settings.

Light source logic 425 is configured to cause light source module 116 to become illuminated in accordance with settings stored in settings storage 415 or received from video monitor 106.

Image capture logic 430 is configured to capture images via camera module 114 based on the most recently updated set of camera settings identified and stored in settings storage 415 and/or received from video monitor 106. The captured images are then forwarded to image output logic 435 for relay to video monitor 106. More specifically, image capture logic 430 is configured to receive image capture control commands from video monitor 106 via data cable 104. In response to an image capture command, image capture logic 430 captures images based on image capture settings stored in settings storage 415. Depending on whether laryngoscope blade 102 is a single-use or reusable blade, image output logic 435 may be integrated within laryngoscope 102 or may include multiple components included within laryngoscope blade 102 and data cable 104.

Figure 5:
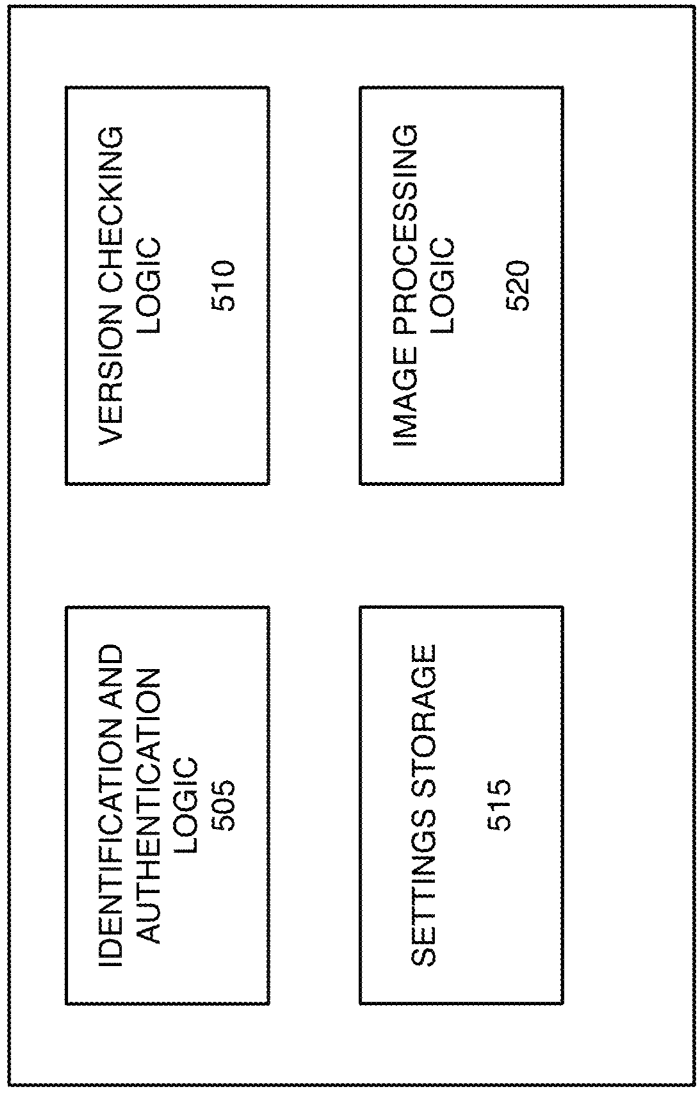
FIG. 5 is an exemplary functional block diagram of components implemented in a data cable consistent with embodiments described herein.

FIG. 5 is an exemplary functional block diagram of components implemented in a data cable 104 in accordance with an embodiment described herein. In the embodiment of FIG. 5, all or some of the components may be implemented by processing unit 320 executing software instructions stored in memory 330.

As shown, data cable 104 may include identification and authentication logic 505, version checking logic 510, and settings storage 515 configured similarly to identification and authentication logic 405, version checking logic 410, and settings storage 415 described above with respect to laryngoscope blade 102. For example, identification and authentication logic 505 may include logic for determining an identity of a connected laryngoscope blade 102. In some implementations, identification and authentication logic 505 may be further configured to determine whether the blade 102 is suitable for use with data cable 104.

Version checking logic 510 includes logic for determining which of data cable 104, video monitor 106, and/or laryngoscope blade 102 has the most up-to-date set of camera settings corresponding to the identified laryngoscope blade 102. As described above in relation to version checking logic 410, version checking logic 510 is similarly configured to alternatively transmit an indication of the version of the set of camera settings stored in settings storage 515 to each of video monitor 106 and laryngoscope blade 102 and similarly receive corresponding information from each of video monitor 106 and laryngoscope blade 102. When it is determined that the version of the set of camera settings stored in settings storage 515 is the most up-to-date, version checking logic 510 may provide the settings to image capture logic 430 in laryngoscope blade 102.

Data cable 104 may further include image processing logic 520 that performs some or all of the image processing on images captured by camera module 114. In one embodiment, image processing logic 520 may include a serializer and/or related logic for preparing images captured by camera module 114 for output and display by video monitor 106.

Figure 6:
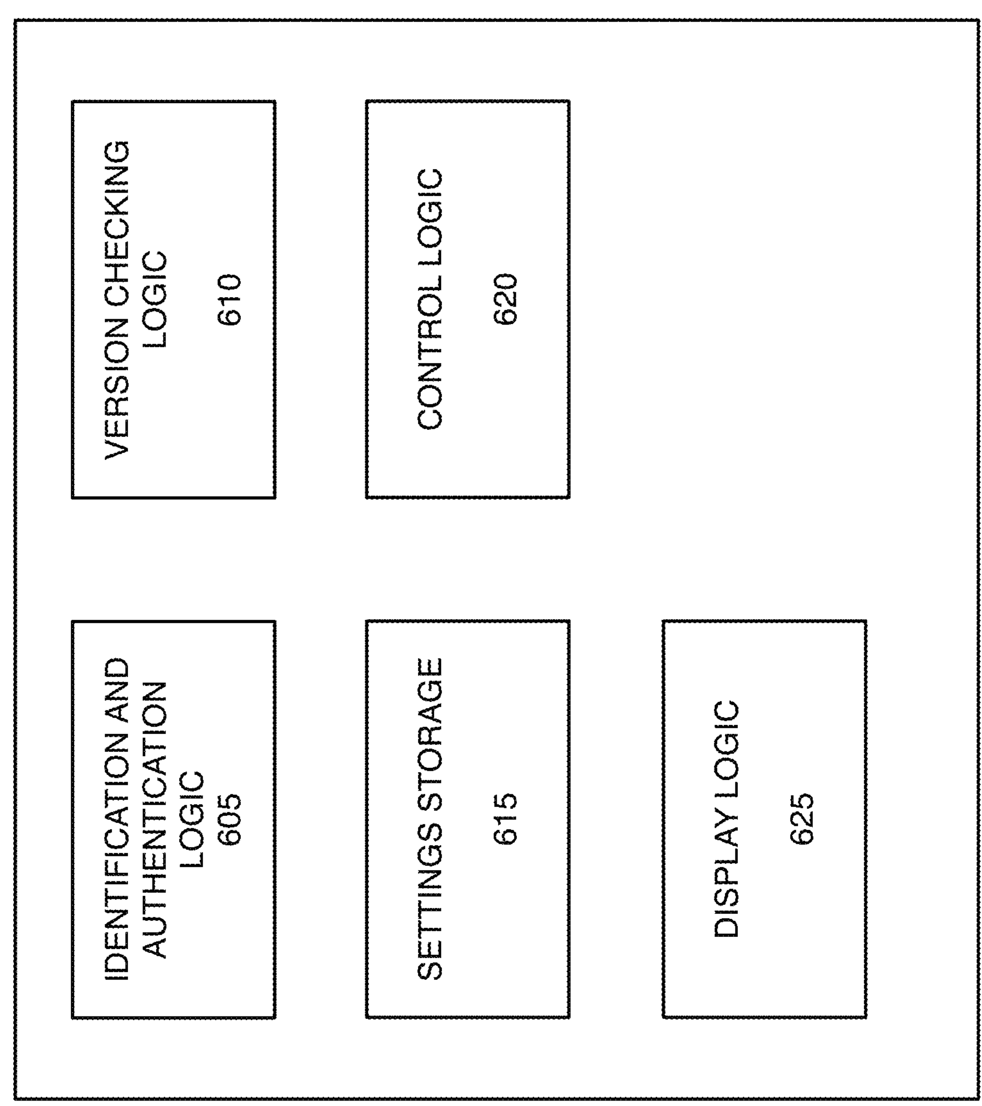
FIG. 6 is an exemplary functional block diagram of components implemented in a video monitor consistent with embodiments described herein.

FIG. 6 is an exemplary functional block diagram of components implemented in a video monitor 106 in accordance with an embodiment described herein. In the embodiment of FIG. 6, all or some of the components may be implemented by processing unit 320 executing software instructions stored in memory 330.

As shown, video monitor 106 may include identification and authentication logic 605, version checking logic 610, settings storage 615, control logic 620, and display logic 625. Identification and authentication logic 605, version checking logic 610, and settings storage 615 may be configured similarly to identification and authentication logic 405/505, version checking logic 410/510, and settings storage 415/515 described above with respect to laryngoscope blade 102 and data cable 104. For example, identification and authentication logic 605 may include logic for determining an identity of a connected laryngoscope blade 102. In some implementations, identification and authentication logic 605 may be further configured to determine whether the blade 102 is suitable for use with video monitor 106.

Version checking logic 610 includes logic for determining which of data cable 104, video monitor 106, and/or laryngoscope blade 102 has the most up-to-date set of camera settings corresponding to the identified laryngoscope blade 102. As described above in relation to version checking logic 410, version checking logic 610 is similarly configured to alternatively transmit an indication of the version of the set of camera settings stored in settings storage 615 to each of data cable 106 and/or laryngoscope blade 102 and similarly receiving corresponding information from each of video monitor 106 and laryngoscope blade 102 before resuming the "master" role on bus 310 (e.g., the $I^2C$ bus). When it is determined that the version of the set of camera settings stored in settings storage 615 is the most up-to-date, version checking logic 610 may provide the settings to image capture logic 430 in laryngoscope blade 102.

After version checking logic 610 completes its check, display logic 625 receives the image data or video signal from laryngoscope blade 102 via data cable 104. As described above, in some implementations, portions of the processing of the image data may be performed by image processing logic 520 in data cable 204.

Consistent with embodiments described herein, the most up-to-date camera settings stored in one of settings storage 415, 515, or 615, may include camera settings optimized for capturing the most useful images in an intra-airway environment. Such an environment typically exhibits the following characteristics: 1) extremely confined field of view, typically having no more than a 3"×3" near circular cavity within which to operate; 2) no primary ambient environmental lighting; all lighting relies on a fixed single point background light emitted by light source module 116 provided immediately adjacent to camera module 114; 3) extreme red spectrum color bias; 4) frequent extreme swings in lighting brightness caused by unpredictable intrusion of objects into camera field of view when combined with the small usage environment; and 5) high contrast with both near-field and far-field points of interest. Unfortunately, conventional camera settings are not optimized for such an environment and, consequently, images or video quality may suffer and/or pertinent visual details may be lost.

As described above, camera module 114 comprises a CCD or CMOS device. Consistent with embodiments described herein, camera module 114 includes a plurality of configurable programming registers that allow the image capturing characteristics of camera module 114 to be optimized. Settings storage 415, 515, and/or 615 in one or more of laryngoscope blade 102, data cable 104, and video monitor 106 may be programmed to include one or more sets of customized camera module register values to optimize image and/or video quality in intra-airway environments. For example, different sets of customized camera module register values may be stored for different identified laryngoscope blades, such as blades for adults, versus pediatric blades, etc.

Modern camera modules generally include automatic gain control (AGC) and/or automatic exposure control (AEC), which are designed to improve image quality by automatically boosting the gain and increasing the exposure in low light images so that objects can be seen more clearly and reduce the gain and decrease the exposure in bright images to avoid the subject of the image from being washed out or blurry. Unfortunately, in intra-airway environments, occluding elements, such as the patient's tongue, an endotracheal tube (ETT), etc. may briefly block the camera view causing the AGC/AEC to reduce the gain and decrease the exposure time, thereby losing far field details, which may be necessary for accurate insertion of the laryngoscope or placement of a corresponding ETT.

Consistent with embodiments described herein, camera module registers or settings relating to the control of AGC and AEC may be optimized. In particular, a setting relating to an upper limit of an AGC/AEC stable operating region may be modified. The upper limit of the AGC/AEC stable operating region refers to how high or bright an incoming image or video signal must become before the camera's gain algorithm mutes or attenuates the signal, by a preset amount, before sending the signal to video monitor 106. Accordingly, consistent with described embodiments, the upper limit of the AGC/AEC stable operating region may be raised (from its default) so that the "trigger point" of upper limit gain attenuation does not occur until the incoming signal significantly increases. The consequence is that any intruding near-field object, such as a patient's tongue or a medical intubation tube, would need to either block a larger portion of the field of view or remain in the field of view much longer.

Consistent with embodiments described herein, a setting relating to the lower limit of the AGC/AEC stable operating region may also be modified. This setting controls how low or dim an incoming signal must achieve before the camera's gain algorithm boosts the signal sent to host. Because a primary objective for intra-airway image capture is to ensure that a patient's far-field vocal chords are visible most of the time during an intubation procedure, the value for the lower limit of the AGC/AEC stable operating region may be increased (from its default) to consequently maintain the "window" in which attenuation is active to a minimum.

In some embodiments, one or more settings relate to or identify the maximum gain boost that can be applied when the incoming signal drops below the AGC/AEC lower limit. As described above, since the AGC/AEC lower limit is raised in accordance with the described embodiments, the effect is that gain boost would be triggered at gain amounts higher than traditionally applied. This may cause images to overexpose even at moderate lighting levels, since the lower limit was now near or above normal lighting levels. To counter this, the automatic gain ceiling maximum AGC value setting may be lowered (from its default) to limit the maximum boost that camera module 114 can apply. This helps manage the over exposure effect and bring it to an acceptable level. Consistent with embodiments described herein, images captured using the above-described optimized settings results in far end vocal cord viewing that is, for example, approximately 25 to 166% brighter than traditional laryngoscope systems. Further, images captured using the above-described optimized settings result in near end reflectance of, for example, approximately 29% over traditional laryngoscope systems. For the overall field of view, images captured using the above-described optimized settings result in a brightness increases of between 50 and 279% over traditional laryngoscope systems for adults and approximately 6.4% for neonatal patients. Additionally, when imaging the vocal cords, the color temperature of the images captured using the optimized settings shifts to the more white/blue light and less red as compared to traditional laryngoscope systems. However, when imaging the overall field, the color temperature shifts to the more red light and less white/blue as compared to traditional laryngoscope systems. Consequently, images captured using the above-described optimized settings yield more a significantly more consistent color temperature.

Figure 7:
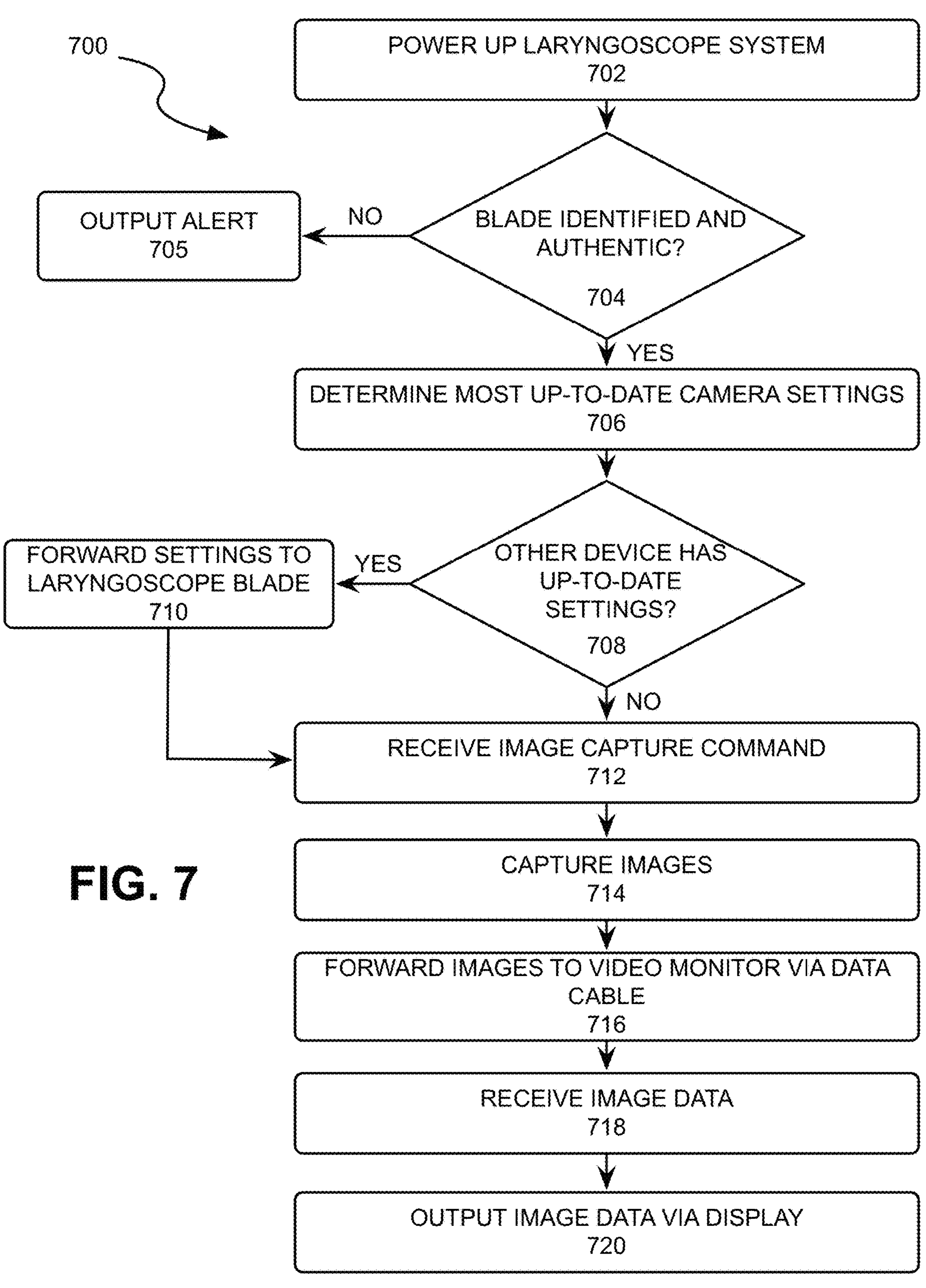
FIG. 7 is a flow diagram illustrating exemplary process for capturing images via the video laryngoscope system of FIG. 1.

FIG. 7 is a flow diagram illustrating an exemplary process 700 for capturing images via video laryngoscope system 100 described herein. In one embodiment, process 700 may begin when laryngoscope blade 102 is plugged into data cable 104, data cable 104 is plugged into video monitor 106, and video monitor 106 is powered up (block 702).

At block 704, data cable 104 and/or video monitor 106 identify laryngoscope blade 102 and determines whether it is authentic. For example, as described above, identification and authentication logic 605 requests and receives blade identification information from laryngoscope blade 102 and determines whether blade 102 is authentic and, potentially, that it has not exceeded its authorized number of uses. If not (block 704—NO), the process ends and a notification or alert is output via video monitor 106 (block 705).

However, if blade 102 is identified and determined to be authentic (block 704—YES), two or more of the laryngoscope blade 102, data cable 104, and video monitor 106 negotiate to determine which device has the most up-to-date camera settings relative to the identified laryngoscope blade 102 (block 706). For example, as described above, each component may alternatively assume a "master" role on bus 310 to receive version information from the other components, which are then compared to its current version.

At block 708, it is determined whether a device other than laryngoscope blade 102 has the most up-to-date settings. If not (block 708—NO), the process proceeds to block 712. However, when one of the other devices includes the most up-to-date settings, (block 708—YES), the settings are forwarded to camera module 114 in laryngoscope blade 102 for use during image capture (block 710).

At block 712, laryngoscope blade 102 receives an image capture command from video monitor 106. For example, image capture logic 430 in laryngoscope blade 102 may receive a request from control logic 620 in video monitor 106. In other embodiments, image capturing may be initiated automatically upon connection of laryngoscope blade 102 to video monitor 106, or via a control on laryngoscope blade 102. In any event, once initiated, image capture logic 430 may capture images based on the settings received or verified in step 708/710 above (block 714).

Captured images are forwarded to video monitor 106 via data cable 104 (block 716). For example, image output logic 435 in laryngoscope blade 102 may output the image data captured by camera module 114 to data cable 104. As described above, in some implementations, some or all image processing on the image data may be performed by image processing logic 520 in data cable 104.

Processed image or video data is received by video monitor 106 (block 718) and output via display 122 (block 720).

The foregoing description of embodiments provides illustration, but is not intended to be exhaustive or to limit the embodiments to the precise form disclosed. In the preceding description, various embodiments have been described with reference to the accompanying drawings. However, various modifications and changes may be made thereto, and additional embodiments may be implemented, without departing from the broader scope of the invention as set forth in the claims that follow. The description and drawings are accordingly to be regarded as illustrative rather than restrictive.

As set forth in this description and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items.

The word "exemplary" is used herein to mean "serving as an example." Any embodiment or implementation described as "exemplary" is not necessarily to be construed as preferred or advantageous over other embodiments or implementations.

Use of ordinal terms such as "first," "second," "third," etc., in the claims to modify a claim element does not by itself connote any priority, precedence, or order of one claim element over another, the temporal order in which acts of a method are performed, the temporal order in which instructions executed by a device are performed, etc., but are used merely as labels to distinguish one claim element having a certain name from another element having a same name (but for use of the ordinal term) to distinguish the claim elements.

No element, act, or instruction described in the present application should be construed as critical or essential to the embodiments described herein unless explicitly described as such.

What is claimed is:

1. A method for updating image capture settings of a video medical device, comprising:

connecting the video medical device to a video monitor via a data cable, wherein two or more of the video medical device, the video monitor, and the data cable each include storage for storing image capture settings;

determining, by at least one of the video monitor or the data cable, an identity of the connected video medical device;

determining which of the video medical device, the video monitor, or the data cable have a most up-to-date set of image capture settings for the identified video medical device;

forwarding the most up-to-date set of image capture settings to the video medical device when it is determined that one of the video monitor or the data cable include the most up-to-date set of image capture settings; and updating the stored image capture settings on the video medical device based on the received most up-to-date set of image capture settings.

2. The method of claim 1, wherein determining which of the video medical device, the video monitor, and the data cable have a most up-to-date set of image capture settings further comprises alternating master and slave roles between the video medical device, the video monitor, and the data cable to pass image capture settings information across a shared bus.

3. The method of claim 1, wherein the video medical device comprises a single use video medical device having image processing capabilities inferior to image processing capabilities for a reusable video medical device, and wherein the data cable comprises image processing logic corresponding to the image processing capabilities of the single use video medical device.

4. The method of claim 1, wherein the most up-to-date image capture settings include optimized automatic gain control (AGC) settings based on the identified video medical device for reducing far field dimming in the presence of a near field obstruction in the field of view.

5. The method of claim 4, wherein the optimized automatic gain control settings comprise:

a value for an upper limit of an AGC stable operating region that is raised from its default value;

a value for a lower limit of an AGC stable operating region that is raised from its default value; and a value for a ceiling of the maximum AGC that is lowered from its default value.

6. The method of claim 1, wherein the most up-to-date image capture settings include optimized color temperature settings based on the identified video medical device.

7. The method of claim 1, wherein determining the identity of the connected video medical device further comprises:

receiving, by at least one of the video monitor or the data cable, identification information from the video medical device; and comparing, by the at least one of the video monitor or the data cable, the received identification information to information stored on the video monitor or data cable and associated with image capture settings.

8. The method of claim 7, wherein the identification information comprises one or more of model or size information.

9. The method of claim 1, further comprising:

storing, by the video medical device, information regarding one or more of: a number of uses of the video medical device, date and time information for the number of uses, or duration of use for the number of uses.

10. The method of claim 9, further comprising:

forwarding the information regarding one or more of: a number of uses of the video medical device, date and time information for the number of uses, or duration of use for the number of uses to at least one of the video monitor or data cable.

11. The method of claim 10, determining, by at least one of the video monitor or the data cable, whether the video medical device may be used based on the received information regarding one or more of: a number of uses of the video medical device, date and time information for the number of uses, or duration of use for the number of uses to at least one of the video monitor or data cable.

* * * * *